United States Patent
Shener

(10) Patent No.: US 9,730,575 B2
(45) Date of Patent: *Aug. 15, 2017

(54) SYSTEM FOR USE IN SURGICAL PROCEDURES

(71) Applicant: Smith & Nephew, Inc., Memphis, TN (US)

(72) Inventor: Cemal Shener, Woburn, MA (US)

(73) Assignee: Smith & Nephew, Inc., Memphis, TN (US)

( * ) Notice: Subject to any disclaimer, the term of this patent is extended or adjusted under 35 U.S.C. 154(b) by 42 days.

This patent is subject to a terminal disclaimer.

(21) Appl. No.: 14/612,402

(22) Filed: Feb. 3, 2015

(65) Prior Publication Data

US 2015/0148605 A1    May 28, 2015

Related U.S. Application Data

(63) Continuation of application No. 13/759,217, filed on Feb. 5, 2013, which is a continuation of application
(Continued)

(51) Int. Cl.
*A61B 1/04* (2006.01)
*A61B 1/12* (2006.01)
(Continued)

(52) U.S. Cl.
CPC .......... *A61B 1/045* (2013.01); *A61B 1/00002* (2013.01); *A61B 1/00006* (2013.01);
(Continued)

(58) Field of Classification Search
CPC .......... A61B 1/015; A61B 1/12; A61B 1/313; A61B 1/00002; A61B 1/00009;
(Continued)

(56) References Cited

U.S. PATENT DOCUMENTS 4,622,584 A    11/1986 Nagasaki et al.
5,368,015 A    11/1994 Wilk
(Continued)

FOREIGN PATENT DOCUMENTS

EP    0340145 A1    11/1989
EP    1911474 A1    2/2013
(Continued)

OTHER PUBLICATIONS

Reexamination Decision No. 87543, Patent Reexamination Board of the State of Intellectual Property Office—P.R. of China; Patent application No. 201080010381.1, date of issue May 4, 2015.
(Continued)

*Primary Examiner* — Rochelle-Ann J Blackman

(57) ABSTRACT

A system and method for use in surgical procedures. The system includes an endoscope, an imaging device coupled to the endoscope, an imaging processor coupled to the imaging device, and at least one management system coupled to the imaging processor, in which a function of the management system is automatically adjusted upon receipt of a communication from the imaging processor.

20 Claims, 1 Drawing Sheet

Related U.S. Application Data

No. 12/710,431, filed on Feb. 23, 2010, now Pat. No. 8,388,515.

(60) Provisional application No. 61/157,391, filed on Mar. 4, 2009.

(51) Int. Cl.

| | | |
|---|---|---|
| *A61B 1/045* | (2006.01) | |
| *A61M 13/00* | (2006.01) | |
| *A61M 5/142* | (2006.01) | |
| *A61B 1/015* | (2006.01) | |
| *A61B 1/313* | (2006.01) | |
| *A61B 1/00* | (2006.01) | |

(52) U.S. Cl.
CPC .......... *A61B 1/00009* (2013.01); *A61B 1/015* (2013.01); *A61B 1/12* (2013.01); *A61B 1/313* (2013.01); *A61M 5/142* (2013.01); *A61M 13/003* (2013.01); *A61M 2005/14208* (2013.01); *A61M 2205/3306* (2013.01); *A61M 2205/3592* (2013.01)

(58) Field of Classification Search
CPC .... A61B 1/00006; A61B 1/045; A61M 5/142; A61M 13/003; A61M 2205/3306; A61M 2205/3592
USPC ........... 600/109, 118, 117, 157, 158; 348/65
See application file for complete search history.

(56) References Cited

U.S. PATENT DOCUMENTS

| 5,868,666 | A | 2/1999 | Okada et al. |
| 5,931,808 | A | 8/1999 | Pike |
| 6,881,188 | B2 | 4/2005 | Furuya et al. |
| 7,479,106 | B2 | 1/2009 | Banik et al. |
| 8,388,515 | B2* | 3/2013 | Shener .................. A61B 1/015 600/109 |
| 2005/0119527 | A1 | 6/2005 | Banik et al. |
| 2006/0047184 | A1 | 3/2006 | Banik et al. |
| 2006/0069306 | A1 | 3/2006 | Banik et al. |
| 2007/0249993 | A1 | 10/2007 | Mollstam et al. |
| 2008/0009747 | A1 | 1/2008 | Saadat et al. |
| 2008/0183080 | A1 | 7/2008 | Abraham |
| 2009/0043167 | A1* | 2/2009 | Leiner .................. A61B 1/3132 600/156 |
| 2010/0130836 | A1* | 5/2010 | Malchano ................ A61B 1/05 600/301 |

FOREIGN PATENT DOCUMENTS

| JP | H03215238 | 9/1991 |
| JP | H11221190 | 8/1999 |
| JP | H11318810 | 11/1999 |
| JP | H11318909 | 11/1999 |
| JP | 2001238205 | 8/2001 |
| WO | WO2006083794 A2 | 8/2006 |
| WO | WO2008028149 A2 | 3/2008 |

OTHER PUBLICATIONS

International Search Report and Written Opinion for PCT/US2010/024978 dated May 7, 2010.
People's Republic of China, First Office Action for Appln. No. 201080010381.1 (PCT/US2010/024978), dated Jul. 29, 2013.
People's Republic of China, Second Office Action for Appln. No. 201080010381.1 (PCT/US2010/024978), dated Mar. 7, 2014.
EPO Communication for Appln. No. 10705252.4-1660, dated Nov. 27, 2013.
Japanese First Office Action/Notice of Reasons for Rejection for Japanese Appln. No. 2011-552974, dated Aug. 20, 2013.
Japanese Second Office Action/Notice of Reasons for Rejection for Japanese Appln. No. 2011-552974, dated Jan. 12, 2014.
Australian Government, Patent Examination Report No. 1 for Patent Application 2010221656, Nov. 28, 2014, pp. 3.
Chinese Second Office Action for Application No. 201510154414.4, issued on Apr. 25, 2016.
Rejection Decision for Chinese Patent Application No. 201510154414.4, issued on Aug. 16, 2016.
First Office Action for Chinese Patent Application No. 201510154414.4, issued on Nov. 23, 2015.

\* cited by examiner

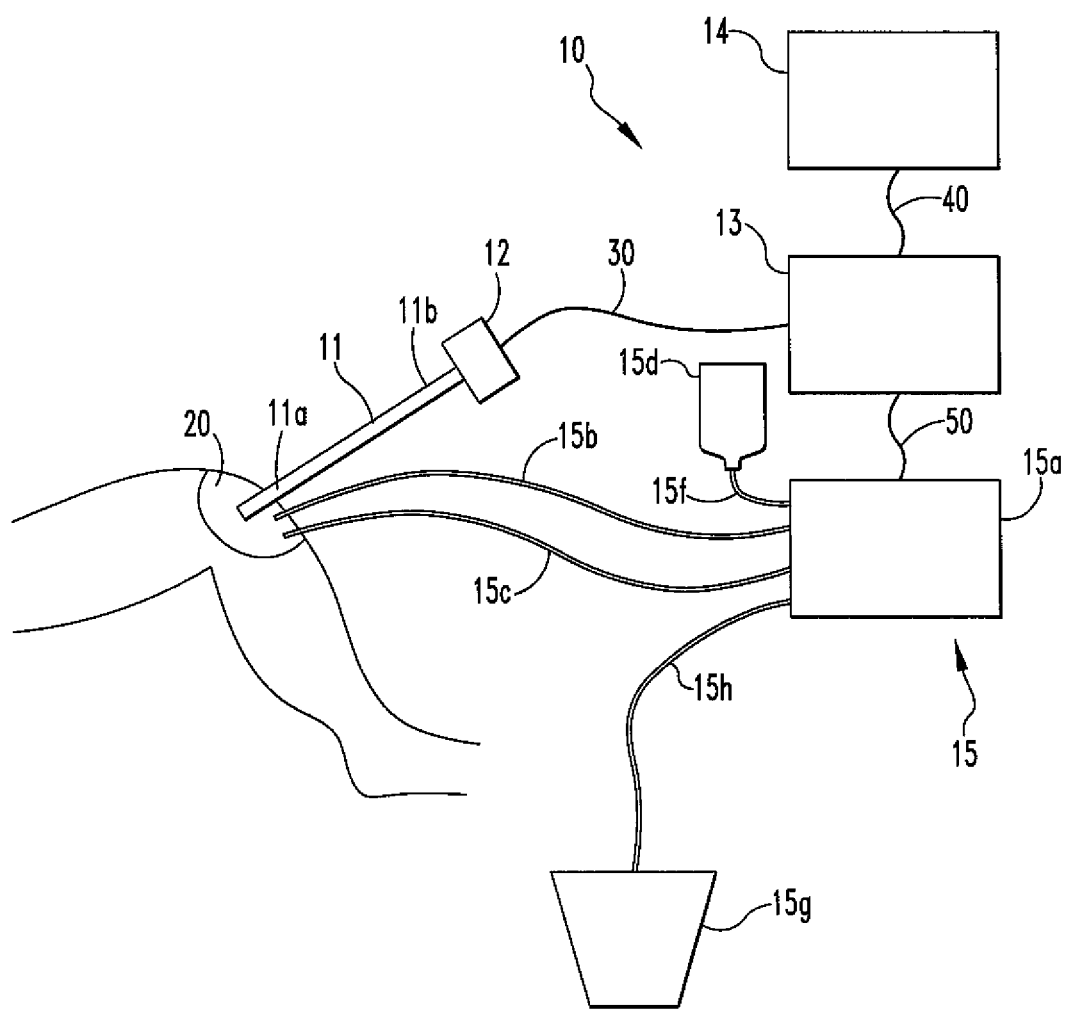

SYSTEM FOR USE IN SURGICAL PROCEDURES

CROSS REFERENCE TO RELATED APPLICATIONS

This patent application is a continuation of U.S. patent application Ser. No. 13/759,217 filed Feb. 5, 2013 entitled SYSTEM FOR USE IN SURGICAL PROCEDURES, which is a continuation of U.S. patent application Ser. No. 12/710,431 filed Feb. 23, 2010 entitled SYSTEM FOR USE IN SURGICAL PROCEDURES, now U.S. Pat. No. 8,388,515, which claims benefit of the priority of U.S. Provisional Patent Application No. 61/157,391 filed Mar. 4, 2009 entitled SYSTEM FOR USE IN SURGICAL PROCEDURES.

TECHNICAL FIELD

The present disclosure relates to systems and methods for use in surgical procedures, such as endoscopic surgical procedures.

BACKGROUND

Currently, during a surgical procedure, such as an endoscopic surgical procedure, an optical image from the surgical site is captured by an endoscope. The image is transmitted to an imaging device, such as a camera, that is coupled to the endoscope, processed, and then transmitted by the device to an imaging processor, such as a camera control unit. The imaging processor further processes the image before transmitting it to a display unit, such as a monitor. The image on the monitor is closely watched by the operating room staff so that when the image becomes unclear, manual adjustments can be made to restore a clear view of the image. For example, when bleeding occurs at the site and the image turns red, the surgeon, or another member of the surgical staff, makes manual adjustments to a fluid management unit, such as a fluid pump, in order to irrigate the site and restore the clear view of the image. This manual activity requires time and resources, thereby extending the amount of time the staff spends performing the surgery.

Therefore, a system is needed that allows for the imaging processor to detect when the image becomes unclear and responds by automatically communicating this information to, for example, a fluid management system, so that automatic adjustments can be made to the fluid management system in order to restore a clear image of the surgical site.

SUMMARY

In accordance with the present disclosure, a system for use in surgical procedures includes an endoscope, an imaging device coupled to the endoscope, an imaging processor coupled to the imaging device, and at least one management system coupled to the imaging processor, wherein a function of the management system is automatically adjusted upon receipt of a communication from the imaging processor.

In one aspect, the endoscope is capable of transmitting an optical image to the imaging device. In one embodiment, the imaging device processes the optical image and transmits the image to the imaging processor. In another embodiment, the system further includes a display unit coupled to the imaging processor, wherein the imaging processor further processes the image and transmits the image to the display unit. In a further embodiment, adjustments to the management system allow for adjustments to the image transmitted to the display unit. In still another embodiment, the imaging device includes a camera. In yet another embodiment, the imaging processor includes a camera control unit. In still yet another embodiment, the at least one management system includes a fluid management system.

In another aspect, a method of adjusting an image of a surgical site during a surgical procedure includes providing an endoscopic system comprising an endoscope, an imaging device coupled to the endoscope, an imaging processor coupled to the imaging device, at least one management system coupled to the imaging processor, and a display unit coupled to the imaging processor, and obtaining an image of the surgical site by viewing the surgical site with the endoscope, the image being transmitted by the imaging processor to the display unit, and automatically adjusting a function of the management system upon receipt of a communication from the imaging processor, wherein adjustments to the function of the management system allow for adjustments to the image on the display unit.

In a further aspect, a system for use with an imaging device and an imaging processor communicably coupled to the imaging device includes an equipment management system communicably coupleable to the imaging processor, wherein the equipment management system having at least one specified function. The specified function of the equipment management system is automatically adjustable upon receipt of a communication from the imaging processor in response to detection of color associated with a material at a target site. The specified function of the equipment management system is further automatically adjustable upon receipt of a communication from the imaging processor in response to detection of an intensity of the color associated with the material at the target site.

Further areas of applicability of the present disclosure will become apparent from the detailed description provided hereinafter. It should be understood that the detailed description and specific examples, while indicating the preferred embodiment of the present disclosure, are intended for purposes of illustration only and are not intended to limit the scope of the disclosure.

BRIEF DESCRIPTION OF THE DRAWINGS

The accompanying drawing, which is incorporated in and form a part of the specification, illustrate an embodiment of the present disclosure and together with the written description serve to explain the principles, characteristics, and features of the disclosure. In the drawing:

FIG. 1 illustrates a first embodiment of an exemplary system for use in surgical procedures, in accordance with the present disclosure.

DETAILED DESCRIPTION OF THE EMBODIMENTS

The disclosures of U.S. patent application Ser. No. 13/759,217 filed Feb. 5, 2013 entitled SYSTEM FOR USE IN SURGICAL PROCEDURES, U.S. patent application Ser. No. 12/710,431 filed Feb. 23, 2010 entitled SYSTEM FOR USE IN SURGICAL PROCEDURES, now U.S. Pat. No. 8,388,515, and U.S. Provisional Patent Application No. 61/157,391 filed Mar. 4, 2009 entitled SYSTEM FOR USE IN SURGICAL PROCEDURES are hereby incorporated herein by reference in their entirety.

The following description of the preferred embodiment(s) is merely exemplary in nature and is in no way intended to limit the invention, its application, or its uses.

FIG. 1 shows a first embodiment of the system 10 of the present disclosure in use during endoscopic surgery. The system 10 includes an endoscope 11 with a first end 11a and a second end 11b. The first end 11a of the endoscope 11 is disposed within a body cavity 20, such as a joint cavity, and an imaging device 12, such as a camera, is coupled to the second end 11b of the endoscope 11. An imaging processor 13, such as a camera control unit, is coupled to the camera 12 via coupling means 30, such as a cable.

Coupled to the imaging processor 13 via separate coupling means 40, 50 are a display unit 14, such as a monitor, and a management system 15, such as a fluid management system. The fluid management system 15 includes a fluid pump 15a and fluid inflow/fluid outflow lines 15b, 15c coupled to the pump 15a. For the purposes of this disclosure, a single cartridge system that includes lines for both the inflow and the outflow is used. The cartridge is coupled to the pump 15a via coupling means. However, other systems may be used. A fluid source 15d, such as a saline bag or other fluid source, is coupled to the pump 15a, via a first tubing 15f and a waste container 15g is coupled to the pump 15a via a second tubing 15h.

During a surgical procedure, an optical image from the surgical site 20 is captured by optical lenses that are located within the endoscope 11. The image is transmitted to the camera 12, specifically to a sensor located within the camera 12, and is processed by the sensor resulting in an analog video signal. The analog video signal is converted to a digital video signal by an analog-to-digital (A/D) converter, also located within the camera 12. The A/D converter may be any suitable analog-to-digital converter known to one of ordinary skill in the art. In addition to the A/D converter, the camera 12 optionally may include a serializer-deserializer (SERDES). If the normal camera readout speed is maintained and the digital video signal is sent to the camera control unit 13 in parallel, an increase in the diameter of the coupling means 30 may be required, which may cause the coupling means 30 to be too large and inflexible. The use of a SERDES substantially reduces this possibility by serializing the signal and increasing the serial transmission rate.

Once the digital video signal is transmitted to the camera control unit 13, the signal is processed by a digital video signal processor located within the unit 13. The processed signal is then transmitted via the coupling means 40 to the monitor.

The digital video signal processor subdivides each field of data, contained within the signal, into regions of interest. Statistical information regarding these regions are provided by the processor to a microprocessor or video processor, which is also contained within the unit 13 and interfaces with the processor via a memory-mapped interface. Other interfaces may also be used. The statistical information includes, but is not limited to, a Red, Green, Blue (RGB) value. The microprocessor converts the RGB value into Hue/Saturation/Value (HSV) via algorithms and other software code that is stored in memory within the microprocessor. Color space other than HSV, such as L*AB, may be converted from the RGB value. Subsequently, the microprocessor uses this HSV information to detect the presence and location of blood at the surgical area 20 by color (Hue), and to determine the concentration of such blood by the intensity of color (saturation). Once the concentration of the blood becomes high enough that the image on the monitor becomes unclear, this unclear image information will be automatically downloaded, via the coupling means 50, by the control unit microprocessor to a microprocessor located in the fluid management system 15.

Upon receipt of this information, a function of the fluid management system 15, such as fluid inflow or fluid outflow, is automatically adjusted to create a clear view of the image. For example, once bleeding occurs at the site 20 and the image turns red, the unit 13 downloads this information to the fluid management system 15, and predetermined adjustments to the pump 15a pressure settings may be made. For example, fluid inflow to the site 20, via the fluid inflow line 15b, may occur in order to irrigate the site 20 and restore the clear view of the image. Alternatively, fluid outflow from the site 20, via the fluid outflow line 15c, may occur in order to withdraw fluid and restore the clear view of the image. These adjusted settings may last for a predetermined length of time and automatically revert to the preceding settings, or the adjusted settings may prevail until such time that the camera control unit 13 detects the level of red within the image to be below a predetermined level, thereby sending a signal to the pump 15a to return its settings to the previous levels.

Furthermore, differential analysis of the statistics by the control unit microprocessor may help to distinguish between static red objects and moving objects, such as blood, at the surgical area 20. The microprocessor may evaluate the statistics per data field and/or process the differential change over multiple data fields to control the rate of fluid inflow and fluid outflow to and from the surgical area 20. Also, once the control unit 13 provides information to the fluid management system 15 that will actuate the system 15 (i.e., cause fluid inflow or fluid outflow to or from the area 20), the system 15 may send a communication to the unit 13 confirming receipt of this information and actuation of the system 15. In this respect, the communication between the control unit 13 and the fluid management system 15 constitutes a closed loop control system. Furthermore, once the unit 13 receives this confirmation, the unit 13 may subsequently send information about this actuation to the monitor 14, such that an on-screen display is showcased on the monitor, thereby allowing the user to know that the system 15 was actuated.

Also, rather than transmitting information via cables 30, 40, 50, the transmission may be wireless via the use of radio frequency technology or other wireless technology. The communication software protocol used by the control unit 13 and the fluid management system 15 to communicate may be, but is not limited to, RS232 or TCP/IP.

In addition to the recognition of redness within the image, other colors or image attributes may be detected by the unit 13 for various other surgical reasons and automatically communicated to the fluid management system 15. Furthermore, other management systems and devices including, but not limited to, shaver control units, radiofrequency generators, and gas insufflators may be coupled to the unit 13 for detection and subsequent communication of attributes for recognition. For instance, a gas insufflator may be coupled to the unit 13 so that, during surgery, debris such as tissue particles and/or air bubbles may be detected by the unit 13 and communicated, via a signal, to the insufflator. Upon receipt of this information by the insufflator, predetermined adjustments to the insufflator pressure settings may be made. For example, inflow of air or some other medical substance to the site 20 may occur in order to free the site 20 of debris and restore the clear view of the image.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A system for use in surgical procedures, comprising:
an endoscope comprising an optical lens located within the endoscope and a camera in an operational relationship with the optical lens and configured to transmit a first plurality of images of a surgical site to a camera control unit;
the camera control unit coupled to the endoscope via a cable and configured to analyze the first plurality of images received from the camera;
a fluid management system that receives a first communication from the camera control unit based on an analysis by the camera control unit, the fluid management system is coupled to the camera control unit, is in fluid communication with the surgical site, and comprises an at least one function associated with a first setting that is automatically adjustable from the first setting to a second setting for a predetermined time upon receipt of the first communication transmitted by the camera control unit and in response to detection by the camera control unit of an intensity of color associated with a material at the surgical site during the analysis of the first plurality of images.

2. The system of claim 1 wherein the function of the surgical equipment management system is further automatically adjustable upon receipt of a second communication in response to a detection by the camera control unit of a level of the color associated with the material at the surgical site relative to a predetermined color level based on a second plurality of images captured via the optical lens.

3. The system of claim 1 wherein the color associated with the material is red.

4. The system of claim 3 wherein the material at the surgical site is blood.

5. The system of claim 1 wherein the fluid management system includes a fluid pump.

6. The system of claim 5 wherein the fluid management system further includes fluid inflow and outflow lines coupleable to the fluid pump.

7. The system of claim 6 wherein the fluid inflow and outflow lines are part of a cartridge system.

8. The system of claim 7 wherein the fluid management system further includes coupling means operative to couple the cartridge system to the fluid pump.

9. The system of claim 5 wherein the fluid pump is coupleable to a fluid source.

10. The system of claim 9 wherein the fluid management system further includes a first tubing operative to couple the fluid pump to the fluid source.

11. The system of claim 5 wherein the fluid pump is coupleable to a waste container.

12. The system of claim 11 wherein the fluid management system further includes a second tubing operative to couple the fluid pump to the waste container.

13. A method for use in surgical procedures comprising:
transmitting, by a camera in an endoscope, a plurality of images of a surgical site, wherein the camera is in an operational relationship with an optical lens inside the endoscope;
receiving, by a camera control unit coupled to the endoscope via a cable, the plurality of images;
analyzing, by the camera control unit, the plurality of images from the surgical site;
receiving, based on the analyzing by the camera control unit, by a fluid management system coupled to the camera control unit and in fluid control with the surgical site, a first communication from the camera control unit;
automatically adjusting in response to receiving the first communication, by the fluid management system, at least one function of the fluid communication system, wherein the first communication comprises a detection by the camera control unit of an intensity of color associated with a material at a surgical site.

14. The method of claim 13 wherein the automatically adjusting of the at least one function of the surgical equipment management system includes automatically adjusting the function of the surgical equipment management system upon receipt of a second communication from the camera control unit in response to detection by the camera control unit of a level of the color associated with the material at the surgical site relative to a predetermined color level.

15. A system comprising:
an endoscope comprising a camera, wherein the endoscope is positioned at a surgical site;
an optical lens located within the endoscope and in an operational relationship with the camera that captures a plurality of images of the surgical site;
an imaging processor coupled to the endoscope via a cable to analyze the plurality of images from the surgical site received from the camera;
a gas insufflator coupled to the imaging processor and in communication with the surgical site, the gas insufflator receives a communication from the imaging processor based on the analysis and the gas insufflator comprises an at least one function that is automatically adjustable upon receipt of the communication from the imaging processor in response to detection by the imaging processor of an intensity of color associated with a material at the surgical site.

16. The system of claim 15, wherein the function of the gas insufflator is automatically adjustable upon the receipt of the communication from the imaging processor in response to the detection by the imaging processor of a saturation of the color associated with the material at the surgical site.

17. The system of claim 15, wherein the function of the equipment management system is automatically adjustable upon the receipt of the communication from the imaging processor in response to the detection by the imaging processor of a saturation of the color associated with the material at the surgical site.

18. A system for use in surgical procedures, comprising:
an endoscope comprising a camera configured to capture a plurality of images of a surgical site via an optical lens located within the endoscope;
an imaging processor coupled to the endoscope via a cable to analyze the plurality of images from the surgical site;
a peripheral device comprising a fluid management system or a gas insufflator coupled to the imaging processor and in communication with the surgical site, the gas insufflator is configured in a first state to receive a communication from the imaging processor based on the analysis, the peripheral device comprises an at least one function that is automatically adjustable upon receipt of the communication from the imaging processor in response to at least one of a first determination by the imaging processor of color associated with a material at a surgical site, and a second determination of an intensity of the color associated with the material at the surgical site.

19. The system of claim 18 wherein the first determination by the imaging processor of the color associated with the material at the surgical site includes a detection by the imaging processor of a hue of the color associated with the material at the surgical site.

20. The system of claim 19 wherein the second determination by the imaging processor of the intensity of the color associated with the material at the surgical site includes a detection by the imaging processor of a saturation of the color associated with the material at the surgical site.

* * * * *